(12) United States Patent
Marsh et al.

(10) Patent No.: US 9,586,063 B2
(45) Date of Patent: Mar. 7, 2017

(54) METHOD OF INHIBITING COPPER DEPOSITION ON HAIR

(71) Applicant: The Procter & Gamble Company, Cincinnati, OH (US)

(72) Inventors: Jennifer Mary Marsh, Mason, OH (US); Casey Patrick Kelly, Wyoming, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 48 days.

(21) Appl. No.: 14/261,684

(22) Filed: Apr. 25, 2014

(65) Prior Publication Data

US 2015/0306430 A1    Oct. 29, 2015

(51) Int. Cl.
*A61Q 5/00*    (2006.01)
*A61K 8/44*    (2006.01)
*A61K 8/49*    (2006.01)
*A61Q 5/02*    (2006.01)
*A61Q 5/12*    (2006.01)

(52) U.S. Cl.
CPC ............... *A61Q 5/002* (2013.01); *A61K 8/44* (2013.01); *A61K 8/4946* (2013.01); *A61Q 5/00* (2013.01); *A61Q 5/006* (2013.01); *A61Q 5/02* (2013.01); *A61Q 5/12* (2013.01); *A61K 2800/10* (2013.01); *A61K 2800/884* (2013.01)

(58) Field of Classification Search
None
See application file for complete search history.

(56) References Cited

U.S. PATENT DOCUMENTS

| | | | |
|---|---|---|---|
| 4,412,943 A | 11/1983 | Hirota | |
| 4,855,130 A | 8/1989 | Konrad | |
| 5,158,684 A | 10/1992 | Moulton | |
| 5,635,167 A | 6/1997 | Said | |
| 5,847,003 A | 12/1998 | Ptchelintsev | |
| 6,129,770 A | 10/2000 | Deutz | |
| 6,287,547 B1 | 9/2001 | Oota | |
| 6,348,189 B1 | 2/2002 | Tanabe | |
| 6,358,502 B1 | 3/2002 | Tanabe | |
| 6,365,143 B1 | 4/2002 | Lundmark | |
| 6,432,394 B2 | 8/2002 | Pyles | |
| 6,451,300 B1* | 9/2002 | Dunlop | A61K 8/0254 424/70.1 |
| 6,509,011 B1 | 1/2003 | Ellis | |
| 6,544,500 B1 | 4/2003 | O'Toole | |
| 6,551,361 B1 | 4/2003 | Cornwell | |
| 6,624,126 B1 | 9/2003 | Kasuga | |
| 7,300,647 B1* | 11/2007 | O'Toole | A61K 8/44 424/401 |
| 7,303,744 B2 | 12/2007 | Wells | |
| 8,349,301 B2 | 1/2013 | Wells | |
| 2003/0176303 A1 | 9/2003 | Niemiec | |
| 2004/0266656 A1 | 12/2004 | Sakurai | |
| 2005/0095215 A1 | 5/2005 | Popp | |
| 2009/0119852 A1 | 5/2009 | Marsh | |
| 2009/0246236 A1* | 10/2009 | Kitko | A61K 8/342 424/401 |
| 2011/0195039 A1 | 8/2011 | Isaacs | |
| 2012/0034181 A1 | 2/2012 | Hoffmann | |
| 2013/0333715 A1 | 12/2013 | Hutton | |

FOREIGN PATENT DOCUMENTS

| | | |
|---|---|---|
| DE | 3929333 A1 | 3/1991 |
| DE | 19943597 A1 | 3/2001 |
| FR | 2853529 A1 | 10/2004 |
| FR | 2853530 A1 | 10/2004 |
| FR | 2853531 A1 | 10/2004 |
| JP | 57109711 A | 7/1982 |
| JP | 5262623 A | 10/1993 |
| JP | 0641579 A | 2/1994 |
| JP | 11180836 A | 7/1999 |
| JP | 2004059540 A | 2/2004 |
| JP | 2006160708 A | 6/2006 |
| JP | 2008169183 A | 7/2008 |
| JP | 2009007283 A | 1/2009 |
| JP | 2011046652 A | 3/2011 |
| JP | 11139941 A | 5/2015 |
| KR | 20090077562 A | 7/2009 |
| WO | 0000170 A1 | 1/2000 |
| WO | 0051555 A1 | 9/2000 |
| WO | 0051556 A1 | 9/2000 |
| WO | 0119327 A1 | 3/2001 |
| WO | 02102302 A2 | 12/2002 |
| WO | 2010124817 A2 | 11/2010 |
| WO | 2014182766 A1 | 11/2014 |

OTHER PUBLICATIONS

U.S. Appl. No. 14/261,668, filed Apr. 25, 2014, Marsh.
U.S. Appl. No. 14/261,705, filed Apr. 25, 2014, Marsh.
PCT Search Report and Written Opinion mailed Jul. 6, 2015, 14 pages.
PCT Search Report and Written Opinion mailed Jul. 14, 2015, 12 pages.
PCT Search Report and Written Opinion mailed Jun. 24, 2015, 12 pages.
PCT Search Report and Written Opinion mailed Jul. 13, 2015, 15 pages.
Meyer; Copper(II)-Histidine Complexes; Journal of American Chemical Society; 92:14; Jul. 15, 1970, 7 pages.
Deschamps; The Saga of Copper(II)-L-Histidine; Coordination Chemistry Reviews 249 (2005) 895-909, 15 pages.
Gould; A Case of Green Hair—a Consequence of Exogenous Copper Deposition and Permanent Waving; Clinical and Experimental Dermatology (1984), 545-553, 9 pages.
www.gnpd.com 2-in-1 Conditioning Shampoo, Record ID 1639748.
www.gnpd.com Shampoo, Record ID 1902817.
www.gnpd.com Shampoo, Record ID 10256242.
www.gnpd.com Color Radiance Shampoo, Record ID 10203234.
www.gnpd.com Shampoo, Record ID 428617.
www.gnpd.com Shampoo for Women of Color, Record ID 579944.

* cited by examiner

*Primary Examiner* — Tigabu Kassa
(74) *Attorney, Agent, or Firm* — James T. Fondriest

(57) ABSTRACT

A method of inhibiting copper deposition on hair and facilitating the removal of copper deposited on hair including applying to the hair a shampoo composition having ethylenediamine-N,N'-disuccinic acid (EDDS) and/or histidine, rinsing the shampoo composition from the hair, applying to the hair a conditioner composition comprising histidine, rinsing the conditioner composition from the hair, and applying to the hair a leave-on treatment comprising ethylenediamine-N,N'-disuccinic acid (EDDS).

14 Claims, No Drawings

METHOD OF INHIBITING COPPER DEPOSITION ON HAIR

FIELD OF THE INVENTION

The present invention relates to a method of inhibiting copper deposition on hair and facilitating the removal of copper deposited on hair.

BACKGROUND OF THE INVENTION

Many water sources that are used by consumers for personal care contain elevated levels of calcium and magnesium salts, as well as undesirable levels of redox metals (e.g., copper and/or iron) salts. As such, using chelants to sequester trace redox metals often proves to be ineffective because most chelants also competitively bind calcium and/or magnesium.

It has been found that even trace quantities of copper can deposit on the hair surface and in between the cuticle layers of hair. This deposition of copper on hair is especially problematic because transition metal ions, such as copper and iron, can facilitate reduction-oxidation (redox) reactions during hair coloring treatments and during UV exposure. These reactions generate reactive oxygen species (ROS), which in turn can cause damage to the hair. In addition, they can interfere with the oxidative color formation chemistry and lead to reduced color uptake for hair colorant users.

Accordingly, there is a need for an improved hair care regimen that can inhibit copper deposition on hair, as well as facilitate the removal of copper already deposited thereon.

SUMMARY OF THE INVENTION

A method of inhibiting copper deposition on hair and facilitating the removal of copper deposited on hair comprising (a) applying to the hair a shampoo composition comprising (i) from about 0.025% to about 0.25% of a compound selected from the group consisting of ethylenediamine-N,N'-disuccinic acid (EDDS), derivatives of ethylenediamine-N,N'-disuccinic acid (EDDS), salts of ethylenediamine-N,N'-disuccinic acid (EDDS), histidine, and mixtures thereof, by weight of the shampoo composition; (ii) from about 2% to about 50% of one or more detersive surfactants, by weight of the shampoo composition; and (iii) from about 20% to about 95% of a first aqueous carrier, by weight of the shampoo composition; (b) rinsing the shampoo composition from the hair; (c) applying to the hair a conditioner composition comprising (i) from about 0.025% to about 0.25% histidine, by weight of the conditioner composition; (ii) a conditioner gel matrix comprising (1) from about 0.1% to about 20% of one or more high melting point fatty compounds, by weight of the conditioner gel matrix; (2) from about 0.1% to about 10% of a cationic surfactant system, by weight of the conditioner gel matrix; and (3) at least 20% of a second aqueous carrier, by weight of the conditioner gel matrix; (d) rinsing the conditioner composition from the hair; and (e) applying to the hair a leave-on treatment comprising (i) from about 0.025% to about 0.25% of a compound selected from the group consisting of ethylenediamine-N,N'-disuccinic acid (EDDS), derivatives of ethylenediamine-N,N'-disuccinic acid (EDDS), salts of ethylenediamine-N,N'-disuccinic acid (EDDS), and mixtures thereof, by weight of the leave-on treatment; (ii) one or more rheology modifiers; and (iii) at least 20% of a third aqueous carrier, by weight of the leave-on treatment.

DETAILED DESCRIPTION OF THE INVENTION

While the specification concludes with claims particularly pointing out and distinctly claiming the invention, it is believed that the present invention will be better understood from the following description.

As used herein, the term "fluid" includes liquids and gels.

As used herein, the term "log x" refers to the common (or decadic) logarithm of x.

As used herein, the articles including "a" and "an" when used in a claim, are understood to mean one or more of what is claimed or described.

As used herein, "comprising" means that other steps and other ingredients which do not affect the end result can be added. This term encompasses the terms "consisting of" and "consisting essentially of".

As used herein, "mixtures" is meant to include a simple combination of materials and any compounds that may result from their combination.

As used herein, "molecular weight" or "M. Wt." refers to the weight average molecular weight unless otherwise stated.

As used herein, the terms "include," "includes," and "including," are meant to be non-limiting and are understood to mean "comprise," "comprises," and "comprising," respectively.

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Unless otherwise noted, all component or composition levels are in reference to the active portion of that component or composition, and are exclusive of impurities, for example, residual solvents or by-products, which may be present in commercially available sources of such components or compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

EDDS & Histidine

Histidine and ethylenediamine-N,N'-disuccinic acid (EDDS) are both chelants. It has been found that histidine and EDDS compounds have the high Formation Constant $K_{ML}$ for copper and the low Formation Constant for calcium that is desired for efficient inhibition of deposition of copper (see Table 1 below) and can be formulated up to a level of 0.25% in shampoos. Histidine and/or EDDS may be present in a shampoo composition, conditioner composition, and/or leave-on treatment at a level of from about 0.025% to about 0.25%, alternatively from about 0.05% to about 0.2%, and alternatively from about 0.1% to about 0.15%, by weight of the shampoo composition, conditioner composition, or leave-on treatment.

The Formation Constant of a metal chelant interaction is defined as:

$$K_{ML} = \frac{[ML]}{[M][L]}$$

where:

[ML]=concentration of metal ligand complex at equilibrium

[M]=concentration of free metal ion

[L]=concentration of free ligand in a fully deprotonated form $K_{ML}$=formation constant for the metal chelant complex. All concentrations are expressed in mol/dm$^3$. Formation Constants are conveniently expressed as logarithms.

TABLE 1

| Amino Acid | Log $K_{ML}$ Cu | Log $K_{ML}$ Ca |
|---|---|---|
| Histidine | 10.2 | 1.2 |
| Asparagine | 7.8 | n/d |
| Tryptophan | 8.2 | n/d |
| Serine | 7.9 | 1.4 |
| Glutamine | 7.7 | n/d |
| Alanine | 8.1 | 1.3 |
| Glycine | 8.2 | 1.1 |
| Proline | 8.8 | n/d |
| EDDS | 18.4 | 4.6 |

The shampoo composition described herein comprises a compound selected from the group consisting of ethylenediamine-N,N'-disuccinic acid (EDDS), derivatives of ethylenediamine-N,N'-disuccinic acid (EDDS), salts of ethylenediamine-N,N'-disuccinic acid (EDDS), histidine, and mixtures thereof at levels sufficient to deliver adequate copper removal performance and to reduce copper uptake into hair. The conditioner composition described herein comprises histidine at levels sufficient to deliver adequate copper removal performance and to reduce copper uptake into hair. The leave-on treatment described herein comprises ethylenediamine-N,N'-disuccinic acid (EDDS), derivatives, and/or salts thereof at levels sufficient to deliver adequate copper removal performance and to reduce copper uptake into hair.

EDDS compounds for use herein may be in the free acid form, and salts thereof. Salts may include alkali metal, alkaline earth metals, and ammonium or substituted ammonium salts. In an embodiment, the salts include sodium, potassium, magnesium, or calcium salts. Examples of sodium salts of EDDS include Na$_2$EDDS and Na$_3$EDDS.

The structure of the acid form of EDDS is as follows:

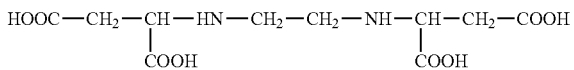

EDDS may be synthesized, for example, from readily available, inexpensive starting materials such as maleic anhydride and ethylenediamine. The synthesis of EDDS from maleic anhydride and ethylene diamine may yield a mixture of three optical isomers, [R,R], [S,S], and [S,R] (25% S,S, 50% R,S and 25% R,R), due to the two asymmetric carbon atoms. The biodegradation of EDDS may be optical isomer-specific, with the [S,S] isomer degrading most rapidly and extensively.

Histidine compounds means compounds according to the general formula below wherein each X is independently selected from substituted or unsubstituted, saturated or unsaturated carbon, preferably unsubstituted and saturated carbon.

n is 0-10, preferably 0-2, more preferably 0.

R1 is selected from hydrogen, alkyl, aryl, arylalkyl or alkaryl, preferably hydrogen or alkyl, more preferably hydrogen.

Y is a heteroatom, preferably nitrogen.

Q is selected from nil, hydrogen, aryl or alkyl, preferably hydrogen.

R3 is selected from hydrogen, alkyl, aryl, arylalkyl or alkaryl, preferably hydrogen or alkyl, more preferably hydrogen.

R4 is independently selected from hydrogen and alkyl, preferably hydrogen.

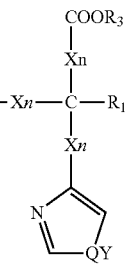

Suitable histidine compounds for use herein include histidine and ester derivatives of histidine. Histidine compounds contain a chiral center and are present in the D- and L-form. For present compositions either form is acceptable as is a mixture of the D- and L-forms.

A person skilled in the art could manufacture histidine compounds using standard techniques. See, for example, *Organic Chemistry, Fifth Edition*, T W Graham Soloman, John Wiley & Son Inc (1992) 1092-1136.

Shampoo Composition

The method of inhibiting copper deposition on hair and facilitating the removal of copper deposited on hair described herein comprises applying to the hair a shampoo composition. The shampoo composition delivers consumer desired shampooing in addition to inhibiting the deposition of copper (i.e. from the water used to rinse) on the hair.

The shampoo composition comprises from about 0.025% to about 0.25%, alternatively from about 0.05% to about 0.2%, alternatively from about 0.1% to about 0.15% of a compound selected from the group consisting of ethylenediamine-N,N'-disuccinic acid (EDDS), derivatives of ethylenediamine-N,N'-disuccinic acid (EDDS), salts of ethylenediamine-N,N'-disuccinic acid (EDDS), histidine, and mixtures thereof, by weight of the shampoo composition. After applying to the hair a shampoo composition as described herein, the method then comprises rinsing the shampoo composition from the hair.

A. Detersive Surfactant

The shampoo composition may comprise one or more detersive surfactants, which provides cleaning performance to the composition. The one or more detersive surfactants in turn may comprise an anionic surfactant, amphoteric or zwitterionic surfactants, or mixtures thereof. Various examples and descriptions of detersive surfactants are set forth in U.S. Pat. No. 6,649,155; U.S. Patent Application Publication No. 2008/0317698; and U.S. Patent Application Publication No. 2008/0206355, which are incorporated herein by reference in their entirety.

The concentration of the detersive surfactant component in the shampoo composition should be sufficient to provide the desired cleaning and lather performance, and generally ranges from about 2 wt % to about 50 wt %, from about 5 wt % to about 30 wt %, from about 8 wt % to about 25 wt %, from about 10 wt % to about 20 wt %, about 5 wt %, about 10 wt %, about 12 wt %, about 15 wt %, about 17 wt %, about 18 wt %, or about 20 wt %.

Anionic surfactants suitable for use in the compositions are the alkyl and alkyl ether sulfates. Other suitable anionic surfactants are the water-soluble salts of organic, sulfuric acid reaction products. Still other suitable anionic surfactants are the reaction products of fatty acids esterified with isethionic acid and neutralized with sodium hydroxide. Other similar anionic surfactants are described in U.S. Pat. Nos. 2,486,921; 2,486,922; and 2,396,278, which are incorporated herein by reference in their entirety.

Exemplary anionic surfactants for use in the shampoo composition include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In a further embodiment, the anionic surfactant is sodium lauryl sulfate or sodium laureth sulfate.

Suitable amphoteric or zwitterionic surfactants for use in the shampoo composition herein include those which are known for use in shampoo or other personal care cleansing. Concentrations of such amphoteric surfactants range from about 0.5 wt % to about 20 wt %, and from about 1 wt % to about 10 wt %. Non limiting examples of suitable zwitterionic or amphoteric surfactants are described in U.S. Pat. Nos. 5,104,646 and 5,106,609, which are incorporated herein by reference in their entirety.

Amphoteric detersive surfactants suitable for use in the shampoo composition include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Exemplary amphoteric detersive surfactants for use in the present shampoo composition include cocoamphoacetate, cocoamphodiacetate, lauroamphoacetate, lauroamphodiacetate, and mixtures thereof.

Zwitterionic detersive surfactants suitable for use in the shampoo composition include those surfactants broadly described as derivatives of aliphatic quaternaryammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. In another embodiment, zwitterionics such as betaines are selected.

Non limiting examples of other anionic, zwitterionic, amphoteric or optional additional surfactants suitable for use in the shampoo composition are described in McCutcheon's, Emulsifiers and Detergents, 1989 Annual, published by M. C. Publishing Co., and U.S. Pat. Nos. 3,929,678, 2,658,072; 2,438,091; 2,528,378, which are incorporated herein by reference in their entirety.

The shampoo composition may also comprise a gel matrix, an aqueous carrier, and other additional ingredients described herein.

B. Aqueous Carrier

The shampoo composition comprises a first aqueous carrier. Accordingly, the formulations of the shampoo composition can be in the form of pourable liquids (under ambient conditions). Such compositions will therefore typically comprise a first aqueous carrier, which is present at a level of at least 20 wt %, from about 20 wt % to about 95 wt %, or from about 60 wt % to about 85 wt %. The first aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The first aqueous carriers useful in the shampoo composition include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

C. Shampoo Gel Matrix

The shampoo composition described herein may comprise a shampoo gel matrix. The shampoo gel matrix comprises (i) from about 0.1% to about 20% of one or more fatty alcohols, alternative from about 0.5% to about 14%, alternatively from about 1% to about 10%, alternatively from about 6% to about 8%, by weight of the shampoo gel matrix; (ii) from about 0.1% to about 10% of one or more shampoo gel matrix surfactants, by weight of the shampoo gel matrix; and (iii) from about 20% to about 95% of a shampoo gel matrix aqueous carrier, alternatively from about 60% to about 85% by weight of the shampoo gel matrix.

The fatty alcohols useful herein are those having from about 10 to about 40 carbon atoms, from about 12 to about 22 carbon atoms, from about 16 to about 22 carbon atoms, or about 16 to about 18 carbon atoms. These fatty alcohols can be straight or branched chain alcohols and can be saturated or unsaturated. Nonlimiting examples of fatty alcohols include, cetyl alcohol, stearyl alcohol, behenyl alcohol, and mixtures thereof. Mixtures of cetyl and stearyl alcohol in a ratio of from about 20:80 to about 80:20 are suitable.

The shampoo gel matrix surfactants may be any of the detersive surfactants described above in section "A."

The shampoo gel matrix aqueous carrier may be any of the aqueous carriers described above in section "B.".

Conditioner Composition

The method of inhibiting copper deposition on hair and facilitating the removal of copper deposited on hair described herein comprises applying to the hair a conditioner composition after rinsing the shampoo composition from the hair. The conditioner composition described herein delivers consumer desired conditioning in addition to inhibiting the deposition of copper (i.e. from the water used to rinse) on the hair.

The conditioner composition described herein comprises (i) from about 0.025% to about 0.25%, alternatively from about 0.05% to about 0.2%, alternatively from about 0.1% to about 0.15% histidine, by weight of the conditioner composition, and (ii) a conditioner gel matrix. The conditioner gel matrix comprises (1) one or more high melting point fatty compounds, (2) a cationic surfactant system, and (3) a second aqueous carrier. After applying to the hair a conditioner composition as described herein, the method then comprises rinsing the conditioner composition from the hair.

A. Cationic Surfactant System

The conditioner gel matrix of the conditioner composition includes a cationic surfactant system. The cationic surfactant system can be one cationic surfactant or a mixture of two or more cationic surfactants. The cationic surfactant system can be selected from: mono-long alkyl quaternized ammonium salt; a combination of mono-long alkyl quaternized ammonium salt and di-long alkyl quaternized ammonium salt; mono-long alkyl amidoamine salt; a combination of mono-long alkyl amidoamine salt and di-long alkyl quaternized ammonium salt, a combination of mono-long alkyl amindoamine salt and mono-long alkyl quaternized ammonium salt.

The cationic surfactant system can be included in the composition at a level by weight of from about 0.1% to about 10%, from about 0.5% to about 8%, from about 0.8% to about 5%, and from about 1.0% to about 4%.

Mono-Long Alkyl Quaternized Ammonium Salt

The monoalkyl quaternized ammonium salt cationic surfactants useful herein are those having one long alkyl chain which has about 22 carbon atoms and in one embodiment a C22 alkyl group. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Mono-long alkyl quaternized ammonium salts useful herein are those having the formula (I):

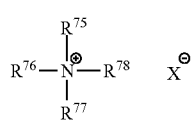

(I)

wherein one of $R^{75}$, $R^{76}$, $R^{77}$ and $R^{78}$ is selected from an alkyl group of 22 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and X⁻ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 22 carbons, or higher, can be saturated or unsaturated. One of $R^{75}$, $R^{76}$, $R^{77}$ and $R^{78}$ can be selected from an alkyl group of about 22 carbon atoms, the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Nonlimiting examples of such mono-long alkyl quaternized ammonium salt cationic surfactants include: behenyl trimethyl ammonium salt.

Mono-Long Alkyl Amidoamine Salt

Mono-long alkyl amines are also suitable as cationic surfactants. Primary, secondary, and tertiary fatty amines are useful. Particularly useful are tertiary amido amines having an alkyl group of about 22 carbons. Exemplary tertiary amido amines include: behenamidopropyldimethylamine, behenamidopropyldiethylamine, behenamidoethyldiethylamine, behenamidoethyldimethylamin. Useful amines in the present invention are disclosed in U.S. Pat. No. 4,275,055, Nachtigal, et al. These amines can also be used in combination with acids such as l-glutamic acid, lactic acid, hydrochloric acid, malic acid, succinic acid, acetic acid, fumaric acid, tartaric acid, citric acid, l-glutamic hydrochloride, maleic acid, and mixtures thereof; in one embodiment l-glutamic acid, lactic acid, and/or citric acid. The amines herein can be partially neutralized with any of the acids at a molar ratio of the amine to the acid of from about 1:0.3 to about 1:2, and/or from about 1:0.4 to about 1:1.

Di-Lone Alkyl Quaternized Ammonium Salt

Di-long alkyl quaternized ammonium salt can be combined with a mono-long alkyl quaternized ammonium salt or mono-long alkyl amidoamine salt. It is believed that such combination can provide easy-to-rinse feel, compared to single use of a monoalkyl quaternized ammonium salt or mono-long alkyl amidoamine salt. In such combination with a mono-long alkyl quaternized ammonium salt or mono-long alkyl amidoamine salt, the di-long alkyl quaternized ammonium salts are used at a level such that the wt % of the dialkyl quaternized ammonium salt in the cationic surfactant system is in the range of from about 10% to about 50%, and/or from about 30% to about 45%.

The di-long alkyl quaternized ammonium salt cationic surfactants useful herein are those having two long alkyl chains having about 22 carbon atoms. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Di-long alkyl quaternized ammonium salts useful herein are those having the formula (II):

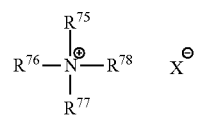

(II)

wherein two of $R^{75}$, $R^{76}$, $R^{77}$ and $R^{78}$ is selected from an alkyl group of from 22 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and X⁻ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 22 carbons, or higher, can be saturated or unsaturated. One of $R^{75}$, $R^{76}$, $R^{77}$ and $R^{78}$ can be selected from an alkyl group of from 22 carbon atoms, the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Such dialkyl quaternized ammonium salt cationic surfactants include, for example, dialkyl (C22) dimethyl ammonium chloride, ditallow alkyl dimethyl ammonium chloride, dihydrogenated tallow alkyl dimethyl ammonium chloride. Such dialkyl quaternized ammonium salt cationic surfactants also include, for example, asymmetric dialkyl quaternized ammonium salt cationic surfactants.

B. High Melting Point Fatty Compound

The conditioner gel matrix of the conditioner composition includes one or more high melting point fatty compounds. The high melting point fatty compounds useful herein may have a melting point of 25° C. or higher, and is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain carbon atoms may have a melting point of less than 25° C. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols are suitable for use in the conditioner composition. The fatty alcohols useful herein are those having from about 14 to about 30 carbon atoms, from about 16 to about 22 carbon atoms. These fatty alcohols are saturated and can be straight or branched chain alcohols. Suitable fatty alcohols include, for example, cetyl alcohol, stearyl alcohol, behenyl alcohol, and mixtures thereof.

High melting point fatty compounds of a single compound of high purity can be used. Single compounds of pure fatty alcohols selected from the group of pure cetyl alcohol, stearyl alcohol, and behenyl alcohol can also be used. By "pure" herein, what is meant is that the compound has a purity of at least about 90%, and/or at least about 95%. These single compounds of high purity provide good rinsability from the hair when the consumer rinses off the composition.

The high melting point fatty compound can be included in the conditioner composition at a level of from about 0.1% to about 20%, alternatively from about 1% to about 15%, and alternatively from about 1.5% to about 8% by weight of the composition, in view of providing improved conditioning benefits such as slippery feel during the application to wet hair, softness and moisturized feel on dry hair.

C. Aqueous Carrier

The conditioner gel matrix of the conditioner composition includes a second aqueous carrier. Accordingly, the formulations of the conditioner composition can be in the form of pourable liquids (under ambient conditions). Such compositions will therefore typically comprise a second aqueous carrier, which is present at a level of from about 20 wt % to about 95 wt %, or from about 60 wt % to about 85 wt %. The second aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The second aqueous carriers useful in the conditioner composition include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

Leave-On Treatment

The method of inhibiting copper deposition on hair and facilitating the removal of copper deposited on hair described herein comprises applying a leave-on treatment to the hair after rinsing the conditioner from the hair. The leave-on treatment described herein delivers consumer desired conditioning in addition to inhibiting the deposition of copper (i.e. from the water used to rinse) on the hair.

The leave-on treatment described herein comprises from about 0.025% to about 0.25%, alternatively from about 0.05% to about 0.2%, alternatively from about 0.1% to about 0.15% of a compound selected from the group consisting of ethylenediamine-N,N'-disuccinic acid (EDDS), derivatives of ethylenediamine-N,N'-disuccinic acid (EDDS), salts of ethylenediamine-N,N'-disuccinic acid (EDDS), and mixtures thereof, by weight of the leave-on treatment. The leave-on treatment also comprises (1) one or more rheology modifiers and (2) a third aqueous carrier.

A. Rheology Modifier

In one embodiment the leave-on treatment may include one or more rheology modifiers to adjust the rheological characteristics of the composition for better feel, in-use properties and the suspending stability of the composition. For example, the rheological properties are adjusted so that the composition remains uniform during its storage and transportation and it does not drip undesirably onto other areas of the body, clothing or home furnishings during its use. Any suitable rheology modifier can be used. In an embodiment, the leave-on treatment may comprise from about 0.01% to about 3% of a rheology modifier, alternatively from about 0.1% to about 1% of a rheology modifier, The one or more rheology modifier may be selected from the group consisting of polyacrylamide thickeners, cationically modified polysaccharidea, associative thickeners, and mixtures thereof. Associative thickeners include a variety of material classes such as, for example: hydrophobically modified cellulose derivatives; hydrophobically modified alkoxylated urethane polymers, such as PEG-150/decyl alcohol/SMDI copolymer, PEG-150/stearyl alcohol/SMDI copolymer, polyurethane-39; hydrophobically modified, alkali swellable emulsions, such as hydrophobically modified polypolyacrylates, hydrophobically modified polyacrylic acids, and hydrophobically modified polyacrylamides; hydrophobic ally modified polyethers. These materials may have a hydrophobe that can be selected from cetyl, stearyl, oleayl, and combinations thereof, and a hydrophilic portion of repeating ethylene oxide groups with repeat units from 10-300, alternatively from 30-200, and alternatively from 40-150. Examples of this class include PEG-120-methylglucose dioleate, PEG-(40 or 60) sorbitan tetraoleate, PEG-150 pentaerythrityl tetrastearate, PEG-55 propylene glycol oleate, PEG-150 distearate.

Non-limiting examples of additional rheology modifiers include acrylamide/ammonium acrylate copolymer (and) polyisobutene (and) polysorbate 20; acrylamide/sodium acryloyldimethyl taurate copolymer/isohexadecane/polysorbate 80; acrylates copolymer; acrylates/beheneth-25 methacrylate copolymer; acrylates/C10-C30 alkyl acrylate crosspolymer; acrylates/steareth-20 itaconate copolymer; ammonium polyacrylate/Isohexadecane/PEG-40 castor oil; C12-16 alkyl PEG-2 hydroxypropylhydroxyethyl ethylcellulose (HM-EHEC); carbomer; crosslinked polyvinylpyrrolidone (PVP); dibenzylidene sorbitol; hydroxyethyl ethylcellulose (EHEC); hydroxypropyl methylcellulose (HPMC); hydroxypropyl methylcellulose (HPMC); hydroxypropylcellulose (HPC); methylcellulose (MC); methylhydroxyethyl cellulose (MEHEC); PEG-150/decyl alcohol/SMDI copolymer; PEG-150/stearyl alcohol/SMDI copolymer; polyacrylamide/C13-14 isoparaffin/laureth-7; polyacrylate 13/polyisobutene/polysorbate 20; polyacrylate crosspolymer-6; polyamide-3; polyquaternium-37 (and) hydrogenated polydecene (and) trideceth-6; polyurethane-39; sodium acrylate/acryloyldimethyltaurate/dimethylacrylamide; crosspolymer (and) isohexadecane (and) polysorbate 60; sodium polyacrylate. Exemplary commercially-available rheology modifiers include ACULYN™ 28, Klucel M CS, Klucel H CS, Klucel G CS, SYLVACLEAR AF1900V, SYLVACLEAR PA1200V, Benecel E10M, Benecel K35M, Optasense RMC70, ACULYN™33, ACULYN™46, ACULYN™22, ACULYN™44, Carbopol Ultrez 20, Carbopol Ultrez 21, Carbopol Ultrez 10, Carbopol 1342, Sepigel™ 305, Simulgel™600, Sepimax Zen, and/or combinations thereof.

B. Aqueous Carrier

The leave-on treatment comprises a third aqueous carrier. Accordingly, the formulations of the leave-on treatment can be in the form of pourable liquids (under ambient conditions). Such compositions will therefore typically comprise a third aqueous carrier, which is present at a level of at least 20 wt %, from about 20 wt % to about 95 wt %, or from about 60 wt % to about 85 wt %. The third aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The third aqueous carriers useful in the leave-on treatment include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

pH

The shampoo composition, conditioner composition, and/or leave-on treatment may have a pH in the range from about 2 to about 10, at 25° C. In an embodiment, the shampoo composition, conditioner composition, and/or leave-on treatment may have a pH in the range of from about 2 to about 6, alternatively from about 5.25 to about 7, which may help to solubilize copper and redox metals already deposited on the hair. Thus, the shampoo composition, conditioner composition, and/or leave-on treatment can also be effective toward washing out the existing copper and redox metals deposits, which can reduce cuticle distortion and thereby reduce cuticle chipping and damage. In an embodiment, the shampoo composition and/or conditioning composition may comprise citric acid, wherein the citric acid acts as a buffer.

Additional Components

The shampoo composition, conditioner composition, and/or leave-on treatment (hair care compositions) described herein may optionally comprise one or more additional components known for use in hair care or personal care products, provided that the additional components are physically and chemically compatible with the essential components described herein, or do not otherwise unduly impair product stability, aesthetics or performance. Such additional components are most typically those described in reference books such as the CTFA Cosmetic Ingredient Handbook, Second Edition, The Cosmetic, Toiletries, and Fragrance Association, Inc. 1988, 1992. Individual concentrations of such additional components may range from about 0.001 wt % to about 10 wt % by weight of the hair care compositions.

Non-limiting examples of additional components for use in the hair care compositions include conditioning agents (e.g., silicones, hydrocarbon oils, fatty esters), natural cationic deposition polymers, synthetic cationic deposition polymers, anti-dandruff agents, particles, suspending agents, paraffinic hydrocarbons, propellants, viscosity modifiers, dyes, non-volatile solvents or diluents (water-soluble and water-insoluble), pearlescent aids, foam boosters, additional surfactants or nonionic cosurfactants, pediculocides, pH adjusting agents, perfumes, preservatives, proteins, skin active agents, sunscreens, UV absorbers, and vitamins.

1. Conditioning Agent

The hair care compositions may comprise one or more conditioning agents. Conditioning agents include materials that are used to give a particular conditioning benefit to hair and/or skin. The conditioning agents useful in the hair care compositions of the present invention typically comprise a water-insoluble, water-dispersible, non-volatile, liquid that forms emulsified, liquid particles. Suitable conditioning agents for use in the hair care composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix.

One or more conditioning agents are present from about 0.01 wt % to about 10 wt %, from about 0.1 wt % to about 8 wt %, and from about 0.2 wt % to about 4 wt %, by weight of the composition.

a. Silicones

The conditioning agent of the hair care compositions may be an insoluble silicone conditioning agent. The silicone conditioning agent particles may comprise volatile silicone, non-volatile silicone, or combinations thereof. In one embodiment the conditioning agent is a non-volatile silicone conditioning agents. If volatile silicones are present, it will typically be incidental to their use as a solvent or carrier for commercially available forms of non-volatile silicone materials ingredients, such as silicone gums and resins. The silicone conditioning agent particles may comprise a silicone fluid conditioning agent and may also comprise other ingredients, such as a silicone resin to improve silicone fluid deposition efficiency or enhance glossiness of the hair.

The concentration of the silicone conditioning agent typically ranges from about 0.01% to about 10%, by weight of the hair care compositions, from about 0.1% to about 8%, from about 0.1% to about 5%, and from about 0.2% to about 3%. Non-limiting examples of suitable silicone conditioning agents, and optional suspending agents for the silicone, are described in U.S. Reissue Pat. No. 34,584, U.S. Pat. No. 5,104,646, and U.S. Pat. No. 5,106,609, which descriptions are incorporated herein by reference. The silicone conditioning agents for use in the hair care compositions may have a viscosity, as measured at 25 Â° C., of from about 20 to about 2,000,000 centistokes ("csk"), from about 1,000 to about 1,800,000 csk, from about 50,000 to about 1,500,000 csk, and from about 100,000 to about 1,500,000 csk.

The dispersed silicone conditioning agent particles typically have a volume average particle diameter ranging from about 0.01 micrometer to about 50 micrometer. For small particle application to hair, the volume average particle diameters typically range from about 0.01 micrometer to about 4 micrometer, from about 0.01 micrometer to about 2 micrometer, from about 0.01 micrometer to about 0.5 micrometer. For larger particle application to hair, the volume average particle diameters typically range from about 5 micrometer to about 125 micrometer, from about 10 micrometer to about 90 micrometer, from about 15 micrometer to about 70 micrometer, from about 20 micrometer to about 50 micrometer.

Background material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989), incorporated herein by reference.

i. Silicone Oils

Silicone fluids include silicone oils, which are flowable silicone materials having a viscosity, as measured at 25° C., less than 1,000,000 csk, from about 5 csk to about 1,000,000 csk, from about 100 csk to about 600,000 csk. Suitable silicone oils for use in the hair care compositions include polyalkyl siloxanes, polyaryl siloxanes, polyalkylaryl siloxanes, polyether siloxane copolymers, and mixtures thereof. Other insoluble, non-volatile silicone fluids having hair conditioning properties may also be used.

Silicone oils include polyalkyl or polyaryl siloxanes which conform to the following Formula (I):

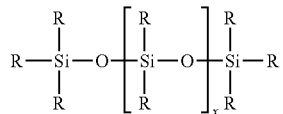

wherein R is aliphatic, in one embodiment alkyl or alkenyl, or aryl, R can be substituted or unsubstituted, and x is an integer from 1 to about 8,000. Suitable R groups for use in the compositions of the present invention include, but are not limited to: alkoxy, aryloxy, alkaryl, arylalkyl, arylalkenyl, alkamino, and ether-substituted, hydroxyl-substituted, and halogen-substituted aliphatic and aryl groups. Suitable R groups also include cationic amines and quaternary ammonium groups.

Suitable alkyl and alkenyl substituents are $C_1$ to $C_5$ alkyls and alkenyls, from $C_1$ to $C_4$, alternatively from $C_1$ to $C_2$. The aliphatic portions of other alkyl-, alkenyl-, or alkynyl-containing groups (such as alkoxy, alkaryl, and alkamino) can be straight or branched chains, and can be from $C_1$ to $C_5$, from $C_1$ to $C_4$, from $C_1$ to $C_3$, from $C_1$ to $C_2$. As discussed above, the R substituents can also contain amino functionalities (e.g. alkamino groups), which can be primary, secondary or tertiary amines or quaternary ammonium. These include mono-, di- and tri-alkylamino and alkoxyamino groups, wherein the aliphatic portion chain length can be as described herein.

ii Amino and Cationic Silicones

Cationic silicone fluids suitable for use in the hair care compositions include, but are not limited to, those which conform to the general formula (II):

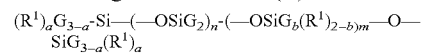

wherein G is hydrogen, phenyl, hydroxy, or $C_1$-$C_8$ alkyl, in one embodiment is methyl; a is 0 or an integer having a value from 1 to 3, in one embodiment 0; b is 0 or 1, in one embodiment 1; n is a number from 0 to 1,999, and in one embodiment from 49 to 499; m is an integer from 1 to 2,000, in one embodiment from 1 to 10; the sum of n and m is a number from 1 to 2,000, in one embodiment from 50 to 500; $R^1$ is a monovalent radical conforming to the general formula $CqH_{2q}L$, wherein q is an integer having a value from 2 to 8 and L is selected from the following groups:

—N($R^2$)CH$_2$—CH$_2$—N($R^2$)$_2$

—N($R^2$)$_2$

—N($R^2$)$_3$A$^-$

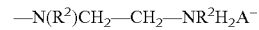

wherein $R^2$ is hydrogen, phenyl, benzyl, or a saturated hydrocarbon radical, in one embodiment an alkyl radical from about $C_1$ to about $C_{20}$, and A$^-$ is a halide ion.

In one embodiment the cationic silicone corresponding to formula (II) is the polymer known as "trimethylsilylamodimethicone", which is shown below in formula (III):

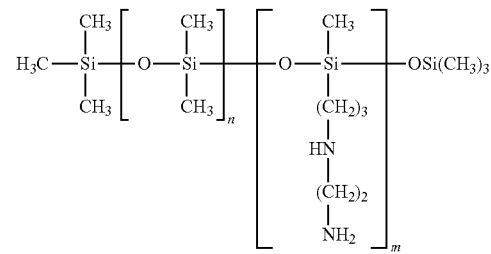

Other silicone cationic polymers which may be used in the hair care compositions described herein are represented by the general formula (IV):

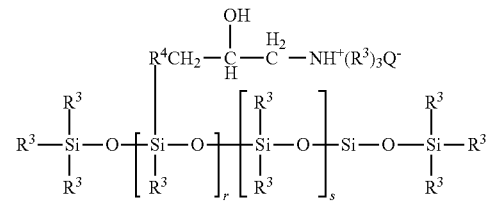

wherein $R^3$ is a monovalent hydrocarbon radical from $C_1$ to $C_{18}$, in one embodiment an alkyl or alkenyl radical, such as methyl; $R_4$ is a hydrocarbon radical, in one embodiment a $C_1$ to $C_{18}$ alkylene radical or a $C_{10}$ to $C_{18}$ alkyleneoxy radical, in one embodiment a $C_1$ to $C_8$ alkyleneoxy radical; $Q^-$ is a halide ion, in one embodiment chloride; r is an average statistical value from 2 to 20, in one embodiment from 2 to 8; s is an average statistical value from 20 to 200, in one embodiment from 20 to 50. One suitable example of a polymer in this class is known as UCARE SILICONE ALE 56®, available from Union Carbide.

iii. Silicone Gums

Other silicone fluids suitable for use in the hair care compositions described herein are the insoluble silicone gums. These gums are polyorganosiloxane materials having a viscosity, as measured at 25° C., of greater than or equal to 1,000,000 csk. Silicone gums are described in U.S. Pat. No. 4,152,416; Noll and Walter, Chemistry and Technology of Silicones, New York: Academic Press (1968); and in General Electric Silicone Rubber Product Data Sheets SE 30, SE 33, SE 54 and SE 76, all of which are incorporated herein by reference. Specific non-limiting examples of silicone gums for use in the compositions of the present invention include polydimethylsiloxane, (polydimethylsiloxane)(methylvinylsiloxane)copolymer, poly(dimethylsiloxane)(diphenyl siloxane)(methylvinylsiloxane)copolymer, and mixtures thereof.

iv. High Refractive Index Silicones

Other non-volatile, insoluble silicone fluid conditioning agents that are suitable for use in the hair care compositions described herein are those known as "high refractive index silicones," having a refractive index of at least about 1.46, at least about 1.48, at least about 1.52, or at least about 1.55. The refractive index of the polysiloxane fluid will generally be less than about 1.70, typically less than about 1.60. In this context, polysiloxane "fluid" includes oils as well as gums. The high refractive index polysiloxane fluid includes those represented by general Formula (I) above, as well as cyclic polysiloxanes such as those represented by Formula (V) below:

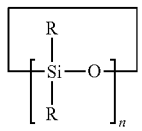

wherein R is as defined above, and n is a number from about 3 to about 7, or from about 3 to about 5.

The high refractive index polysiloxane fluids contain an amount of aryl-containing R substituents sufficient to increase the refractive index to the desired level, which is described herein. Additionally, R and n must be selected so that the material is non-volatile.

Aryl-containing substituents include those which contain alicyclic and heterocyclic five and six member aryl rings and those which contain fused five or six member rings. The aryl rings themselves can be substituted or unsubstituted.

Generally, the high refractive index polysiloxane fluids may have a degree of aryl-containing substituents of at least about 15%, at least about 20%, at least about 25%, at least about 35%, at least about 50%. Typically, the degree of aryl substitution will be less than about 90%, more generally less than about 85%, and in one embodiment from about 55% to about 80%.

Suitable high refractive index polysiloxane fluids may have a combination of phenyl or phenyl derivative substituents, with alkyl substituents, in one embodiment $C_1$-$C_4$ alkyl (in one embodiment methyl), hydroxy, or $C_1$-$C_4$ alkylamino (especially —$R^4NHR^5NH2$ wherein each $R^4$ and $R^5$ independently is a $C_1$-$C_3$ alkyl, alkenyl, and/or alkoxy).

When high refractive index silicones are used in the hair care compositions described herein, they can be used in solution with a spreading agent, such as a silicone resin or a surfactant, to reduce the surface tension by a sufficient amount to enhance spreading and thereby enhance the glossiness (subsequent to drying) of hair treated with the hair care compositions.

Silicone fluids suitable for use in the hair care compositions described herein are disclosed in U.S. Pat. No. 2,826,551, U.S. Pat. No. 3,964,500, U.S. Pat. No. 4,364,837, British Pat. No. 849,433, and Silicon Compounds, Petrarch Systems, Inc. (1984), all of which are incorporated herein by reference.

v. Silicone Resins

Silicone resins may be included in the silicone conditioning agent of the hair care compositions described herein. These resins are highly cross-linked polymeric siloxane systems. The cross-linking is introduced through the incorporation of trifunctional and tetrafunctional silanes with monofunctional or difunctional, or both, silanes during manufacture of the silicone resin.

Silicone materials and silicone resins in particular, can conveniently be identified according to a shorthand nomenclature system known to those of ordinary skill in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadra- or tetrafunctional unit $SiO_2$. Primes of the unit symbols (e.g. M', D', T', and Q') denote substituents other than methyl, and must be specifically defined for each occurrence.

Suitable silicone resins for use in the hair care compositions described herein include, but are not limited to MQ, MT, MTQ, MDT and MDTQ resins. Methyl is a suitable silicone substituent. Other suitable silicone resins include MQ resins, wherein the M:Q ratio is from about 0.5:1.0 to about 1.5:1.0 and the average molecular weight of the silicone resin is from about 1000 to about 10,000.

The weight ratio of the non-volatile silicone fluid, having refractive index below 1.46, to the silicone resin component, when used, can be from about 4:1 to about 400:1, from about 9:1 to about 200:1, from about 19:1 to about 100:1, particularly when the silicone fluid component is a polydimethylsiloxane fluid or a mixture of polydimethylsiloxane fluid and polydimethylsiloxane gum as described herein. Insofar as the silicone resin forms a part of the same phase in the compositions hereof as the silicone fluid, i.e. the conditioning active, the sum of the fluid and resin should be included in determining the level of silicone conditioning agent in the hair care compositions.

b. Organic Conditioning Oils

The conditioning agent of the hair care compositions described herein may also comprise at least one organic conditioning oil, either alone or in combination with other conditioning agents, such as the silicones described above.

i. Hydrocarbon Oils

Suitable organic conditioning oils for use as conditioning agents in hair care compositions include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils can be from about $C_{12}$ to about $C_{19}$. Branched chain hydrocarbon oils, including hydrocarbon polymers, typically will contain more than 19 carbon atoms.

ii. Polyolefins

Organic conditioning oils for use in the hair care compositions described herein also include liquid polyolefins, including liquid poly-α-olefins and/or hydrogenated liquid poly-α-olefins. Polyolefins for use herein are prepared by polymerization of $C_4$ to about $C_{14}$ olefenic monomers, and in one embodiment from about $C_6$ to about $C_{12}$.

iii. Fatty Esters

Other suitable organic conditioning oils for use as a conditioning agent in the hair care compositions described herein include fatty esters having at least 10 carbon atoms. These fatty esters include esters with hydrocarbyl chains derived from fatty acids or alcohols. The hydrocarbyl radicals of the fatty esters hereof may include or have covalently bonded thereto other compatible functionalities, such as amides and alkoxy moieties (e.g., ethoxy or ether linkages, etc.).

iv. Fluorinated Conditioning Compounds

Fluorinated compounds suitable for delivering conditioning to hair or skin as organic conditioning oils include perfluoropolyethers, perfluorinated olefins, fluorine based specialty polymers that may be in a fluid or elastomer form similar to the silicone fluids previously described, and perfluorinated dimethicones.

v. Fatty Alcohols

Other suitable organic conditioning oils for use in the hair care compositions described herein include, but are not limited to, fatty alcohols having at least about 10 carbon atoms, about 10 to about 22 carbon atoms, and in one embodiment about 12 to about 16 carbon atoms.

vi. Alkyl Glucosides and Alkyl Glucoside Derivatives

Suitable organic conditioning oils for use in the hair care compositions described herein include, but are not limited to, alkyl glucosides and alkyl glucoside derivatives. Specific non-limiting examples of suitable alkyl glucosides and alkyl glucoside derivatives include Glucam E-10, Glucam E-20, Glucam P-10, and Glucquat 125 commercially available from Amerchol.

c. Other Conditioning Agents i. Quaternary Ammonium Compounds

Suitable quaternary ammonium compounds for use as conditioning agents in the hair care compositions described herein include, but are not limited to, hydrophilic quaternary ammonium compounds with a long chain substituent having a carbonyl moiety, like an amide moiety, or a phosphate ester moiety or a similar hydrophilic moiety.

Examples of useful hydrophilic quaternary ammonium compounds include, but are not limited to, compounds designated in the CTFA Cosmetic Dictionary as ricinoleamidopropyl trimonium chloride, ricinoleamido trimonium ethylsulfate, hydroxy stearamidopropyl trimoniummethylsulfate and hydroxy stearamidopropyl trimonium chloride, or combinations thereof.

ii. Polyethylene Glycols

Additional compounds useful herein as conditioning agents include polyethylene glycols and polypropylene glycols having a molecular weight of up to about 2,000,000 such as those with CTFA names PEG-200, PEG-400, PEG-600, PEG-1000, PEG-2M, PEG-7M, PEG-14M, PEG-45M and mixtures thereof.

iii. Cationic Deposition Polymers

The hair care compositions described herein may further comprise a cationic deposition polymer. Any known natural or synthetic cationic deposition polymer can be used herein. Examples include those polymers disclosed in U.S. Pat. No. 6,649,155; U.S. Patent Application Publication Nos. 2008/0317698; 2008/0206355; and 2006/0099167, which are incorporated herein by reference in their entirety.

The cationic deposition polymer is included in the composition at a level from about 0.01 wt % to about 2 wt %, in one embodiment from about 1.5 wt % to about 1.9 wt %, in another embodiment from about 1.8 wt % to about 2.0 wt %, in view of providing the benefits of the present invention.

The cationic deposition polymer is a water soluble polymer with a charge density from about 0.5 milliequivalents per gram to about 12 milliequivalents per gram. The cationic deposition polymer used in the composition has a molecular weight of about 100,000 Daltons to about 5,000,000 Daltons. The cationic deposition polymer is a low charge density cationic polymer.

In one embodiment, the cationic deposition polymer is a synthetic cationic deposition polymer. A variety of synthetic cationic deposition polymers can be used including mono- and di-alkyl chain cationic surfactants. In one embodiment, mono-alkyl chain cationic surfactants are chosen including, for example, mono-alkyl quaternary ammonium salts and mono-alkyl amines. In another embodiment, di-alkyl chain cationic surfactants are used and include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, dicetyl dimethyl ammonium chloride, and mixtures thereof.

In another embodiment, the cationic deposition polymer is a naturally derived cationic polymer. The term, "naturally derived cationic polymer" as used herein, refers to cationic deposition polymers which are obtained from natural sources. The natural sources may be polysaccharide polymers. Therefore, the naturally derived cationic polymer may be selected from the group comprising starches, guar, cellulose, Cassia, locust bean, Konjac, Tara, galactomannan, tapioca, and synthetic polymers. In a further embodiment, cationic deposition polymers are selected from Mirapol® 100S (Rhodia), Jaguar® C17, polyDADMAC, Tapioca starch (Akzo), Triquat™, and mixtures thereof.

d. Anionic Emulsifiers

A variety of anionic emulsifiers can be used in the hair care compositions described herein. The anionic emulsifiers include, by way of illustrating and not limitation, water-soluble salts of alkyl sulfates, alkyl ether sulfates, alkyl isothionates, alkyl carboxylates, alkyl sulfosuccinates, alkyl succinamates, alkyl sulfate salts such as sodium dodecyl sulfate, alkyl sarcosinates, alkyl derivatives of protein hydrolyzates, acyl aspartates, alkyl or alkyl ether or alkylaryl ether phosphate esters, sodium dodecyl sulphate, phospholipids or lecithin, or soaps, sodium, potassium or ammonium stearate, oleate or palmitate, alkylarylsulfonic acid salts such as sodium dodecylbenzenesulfonate, sodium dialkylsulfosuccinates, dioctyl sulfosuccinate, sodium dilaurylsulfosuccinate, poly(styrene sulfonate) sodium salt, isobutylene-maleic anhydride copolymer, gum arabic, sodium alginate, carboxymethylcellulose, cellulose sulfate and pectin, poly(styrene sulfonate), isobutylene-maleic anhydride copolymer, gum arabic, carrageenan, sodium alginate, pectic acid, tragacanth gum, almond gum and agar; semi-synthetic polymers such as carboxymethyl cellulose, sulfated cellulose, sulfated methylcellulose, carboxymethyl starch, phosphated starch, lignin sulfonic acid; and synthetic polymers such as maleic anhydride copolymers (including hydrolyzates thereof), polyacrylic acid, polymethacrylic acid, acrylic acid butyl acrylate copolymer or crotonic acid homopolymers and copolymers, vinylbenzenesulfonic acid or 2-acrylamido-2-methylpropanesulfonic acid homopolymers and copolymers, and partial amide or partial ester of such polymers and copolymers, carboxymodified polyvinyl alcohol, sulfonic acid-modified polyvinyl alcohol and phosphoric acid-modified polyvinyl alcohol, phosphated or sulfated tristyrylphenol ethoxylates.

In addition, anionic emulsifiers that have acrylate functionality may also be used in the hair care compositions described herein. Anionic emulsifiers useful herein include, but aren't limited to: poly(meth)acrylic acid; copolymers of (meth)acrylic acids and its (meth)acrylates with C1-22 alkyl, C1-C8 alkyl, butyl; copolymers of (meth)acrylic acids and (meth)acrylamide; Carboxyvinylpolymer; acrylate copolymers such as Acrylate/C10-30 alkyl acrylate crosspolymer, Acrylic acid/vinyl ester copolymer/Acrylates/Vinyl Isodecanoate crosspolymer, Acrylates/Palmeth-25 Acrylate copolymer, Acrylate/Steareth-20 Itaconate copolymer, and Acrylate/Celeth-20 Itaconate copolymer; Polystyrene sulphonate, copolymers of methacrylic acid and acrylamidomethylpropane sulfonic acid, and copolymers of acrylic acid and acrylamidomethylpropane sulfonic acid; carboxymethycellulose; carboxy guar; copolymers of ethylene and maleic acid; and acrylate silicone polymer. Neutralizing agents may be included to neutralize the anionic emulsifiers herein. Non-limiting examples of such neutralizing agents include sodium hydroxide, potassium hydroxide, ammonium hydroxide, monoethanolamine, diethanolamine, triethanolamine, diisopropanolamine, aminomethylpropanol, tromethamine, tetrahydroxypropyl ethylenediamine, and mixtures thereof. Commercially available anionic emulsifiers include, for example, Carbomer supplied from Noveon under the tradename Carbopol 981 and Carbopol 980; Acrylates/C10-30 Alkyl Acrylate Crosspolymer having tradenames Pemulen TR-1, Pemulen TR-2, Carbopol 1342, Carbopol 1382, and Carbopol ETD 2020, all available from Noveon; sodium carboxymethylcellulose supplied from Hercules as CMC series; and Acrylate copolymer having a tradename Capigel supplied from Seppic. In another embodiment, anionic emulsifiers are carboxymethylcelluloses.

e. Benefit Agents

The benefit agents comprise a material selected from the group consisting of anti-dandruff agents; perfumes; brighteners; enzymes; perfumes; sensates in one aspect a cooling agent; attractants, anti-bacterial agents; dyes; pigments; bleaches; and mixtures thereof.

In one aspect said benefit agent may comprise an anti-dandruff agent. Such anti-dandruff particulate should be physically and chemically compatible with the essential components of the composition, and should not otherwise unduly impair product stability, aesthetics or performance.

According to an embodiment, the hair care compositions may comprise an anti-dandruff active, which may be an anti-dandruff active particulate. In an embodiment, the anti-dandruff active is selected from the group consisting of: pyridinethione salts; azoles, such as ketoconazole, econazole, and elubiol; selenium sulphide; particulate sulfur; keratolytic agents such as salicylic acid; and mixtures thereof. In an embodiment, the anti-dandruff particulate is a pyridinethione salt.

Pyridinethione particulates are suitable particulate anti-dandruff actives. In an embodiment, the anti-dandruff active is a 1-hydroxy-2-pyridinethione salt and is in particulate form. In an embodiment, the concentration of pyridinethione anti-dandruff particulate ranges from about 0.01 wt % to about 5 wt %, or from about 0.1 wt % to about 3 wt %, or from about 0.1 wt % to about 2 wt %. In an embodiment, the pyridinethione salts are those formed from heavy metals such as zinc, tin, cadmium, magnesium, aluminium and zirconium, generally zinc, typically the zinc salt of 1-hydroxy-2-pyridinethione (known as "zinc pyridinethione" or "ZPT"), commonly 1-hydroxy-2-pyridinethione salts in platelet particle form. In an embodiment, the 1-hydroxy-2-pyridinethione salts in platelet particle form have an average particle size of up to about 20 microns, or up to about 5 microns, or up to about 2.5 microns. Salts formed from other cations, such as sodium, may also be suitable. Pyridinethione anti-dandruff actives are described, for example, in U.S. Pat. No. 2,809,971; U.S. Pat. No. 3,236,733; U.S. Pat. No. 3,753,196; U.S. Pat. No. 3,761,418; U.S. Pat. No. 4,345,080; U.S. Pat. No. 4,323,683; U.S. Pat. No. 4,379,753; and U.S. Pat. No. 4,470,982.

In an embodiment, in addition to the anti-dandruff active selected from polyvalent metal salts of pyrithione, the hair care compositions may further comprise one or more anti-fungal and/or anti-microbial actives. In an embodiment, the anti-microbial active is selected from the group consisting of: coal tar, sulfur, charcoal, whitfield's ointment, castellani's paint, aluminum chloride, gentian violet, octopirox (piroctone olamine), ciclopirox olamine, undecylenic acid and its metal salts, potassium permanganate, selenium sulphide, sodium thiosulfate, propylene glycol, oil of bitter orange, urea preparations, griseofulvin, 8-hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone, and azoles, and mixtures thereof. In an embodiment, the anti-microbial is selected from the group consisting of: itraconazole, ketoconazole, selenium sulphide, coal tar, and mixtures thereof.

In an embodiment, the azole anti-microbials is an imidazole selected from the group consisting of: benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and mixtures thereof, or the azole anti-microbials is a triazole selected from the group consisting of: terconazole, itraconazole, and mixtures thereof. When present in the hair care composition, the azole anti-microbial active is included in an amount of from about 0.01 wt % to about 5 wt %, or from about 0.1 wt % to about 3 wt %, or from about 0.3 wt % to about 2 wt %. In an embodiment, the azole anti-microbial active is ketoconazole. In an embodiment, the sole anti-microbial active is ketoconazole.

The hair care compositions described herein may also comprise a combination of anti-microbial actives. In an embodiment, the combination of anti-microbial active is selected from the group of combinations consisting of: octopirox and zinc pyrithione, pine tar and sulfur, salicylic acid and zinc pyrithione, salicylic acid and elubiol, zinc pyrithione and elubiol, zinc pyrithione and climbasole, octopirox and climbasole, salicylic acid and octopirox, and mixtures thereof.

In an embodiment, the hair care compositions may comprise an effective amount of a zinc-containing layered material. In an embodiment, the composition comprises from about 0.001 wt % to about 10 wt %, or from about 0.01 wt % to about 7 wt %, or from about 0.1 wt % to about 5 wt % of a zinc-containing layered material, by total weight of the hair care composition.

Zinc-containing layered materials may be those with crystal growth primarily occurring in two dimensions. It is conventional to describe layer structures as not only those in which all the atoms are incorporated in well-defined layers, but also those in which there are ions or molecules between the layers, called gallery ions (A. F. Wells "Structural Inorganic Chemistry" Clarendon Press, 1975) Zinc-containing layered materials (ZLMs) may have zinc incorporated in the layers and/or be components of the gallery ions. The following classes of ZLMs represent relatively common examples of the general category and are not intended to be limiting as to the broader scope of materials which fit this definition.

Many ZLMs occur naturally as copper. In an embodiment, the ZLM is selected from the group consisting of: hydrozincite (zinc carbonate hydroxide), aurichalcite (zinc copper carbonate hydroxide), rosasite (copper zinc carbonate hydroxide), and mixtures thereof. Related copper that are zinc-containing may also be included in the composition. Natural ZLMs can also occur wherein anionic layer species such as clay-type copper (e.g., phyllosilicates) contain ion-exchanged zinc gallery ions. All of these natural materials can also be obtained synthetically or formed in situ in a composition or during a production process.

Another common class of ZLMs, which are often, but not always, synthetic, is layered double hydroxides. In an embodiment, the ZLM is a layered double hydroxide conforming to the formula $[M^{2+}_{1-x}M^{3+}_{x}(OH)_2]^{x+}A^{m-}_{x/m}\cdot nH_2O$ wherein some or all of the divalent ions ($M^{2+}$) are zinc ions (Crepaldi, E L, Pava, P C, Tronto, J, Valim, J B *J. Colloid Interfac. Sci.* 2002, 248, 429-42).

Yet another class of ZLMs can be prepared called hydroxy double salts (Morioka, H., Tagaya, H., Karasu, M, Kadokawa, J, Chiba, K *Inorg. Chem.* 1999, 38, 4211-6). In an embodiment, the ZLM is a hydroxy double salt conforming to the formula $[M^{2+}_{1-x}M^{2+}_{1+x}(OH)_{3(1-y)}]^{+}A^{n-}_{(1=3y)/n}\cdot nH_2O$ where the two metal ions ($M^{2+}$) may be the same or different. If they are the same and represented by zinc, the formula simplifies to $[Zn_{1+x}(OH)_2]^{2x+}2xA^{-}\cdot nH_2O$. This latter formula represents (where x=0.4) materials such as zinc hydroxychloride and zinc hydroxynitrate. In an embodiment, the ZLM is zinc hydroxychloride and/or zinc hydroxynitrate. These are related to hydrozincite as well wherein a divalent anion replaces the monovalent anion. These materials can also be formed in situ in a composition or in or during a production process.

In embodiments having a zinc-containing layered material and a pyrithione or polyvalent metal salt of pyrithione, the ratio of zinc-containing layered material to pyrithione or a polyvalent metal salt of pyrithione may be from about 5:100 to about 10:1, or from about 2:10 to about 5:1, or from about 1:2 to about 3:1.

The on-scalp deposition of the anti-dandruff active may be at least about 1 microgram/cm². The on-scalp deposition of the anti-dandruff active is important in view of ensuring that the anti-dandruff active reaches the scalp where it is able to perform its function. In an embodiment, the deposition of the anti-dandruff active on the scalp is at least about 1.5 microgram/cm², or at least about 2.5 microgram/cm², or at least about 3 microgram/cm², or at least about 4 microgram/cm², or at least about 6 microgram/cm², or at least about 7 microgram/cm², or at least about 8 microgram/cm², or at least about 8 microgram/cm², or at least about 10 microgram/cm². The on-scalp deposition of the anti-dandruff active is measured by having the hair of individuals washed with a composition comprising an anti-dandruff active, for example a composition pursuant to the present invention, by trained a cosmetician according to a conventional washing protocol. The hair is then parted on an area of the scalp to allow an open-ended glass cylinder to be held on the surface while an aliquot of an extraction solution is added and agitated prior to recovery and analytical determination of anti-dandruff active content by conventional methodology, such as HPLC.

The hair care compositions of the present invention may be presented in typical hair care formulations. They may be in the form of solutions, dispersion, emulsions, powders, talcs, encapsulated, spheres, spongers, solid dosage forms, foams, and other delivery mechanisms. The compositions of the embodiments of the present invention may be hair tonics, leave-on hair products such as treatment, and styling products, rinse-off hair products such as shampoos, and treatment products; and any other form that may be applied to hair.

According to one embodiment, the hair care compositions may be provided in the form of a porous, dissolvable solid structure, such as those disclosed in U.S. Patent Application Publication Nos. 2009/0232873; and 2010/0179083, which are incorporated herein by reference in their entirety. Accordingly, the hair care compositions comprise a chelant, a buffer system comprising an organic acid, from about 23% to about 75% surfactant; from about 10% to about 50% water soluble polymer; and optionally, from about 1% to about 15% plasticizer; such that the hair care composition is in the form of a flexible porous dissolvable solid structure, wherein said structure has a Percent open cell content of from about 80% to about 100%.

According to another embodiment, the hair care compositions may be in the form of a porous dissolvable solid structure comprising a chelant; a buffer system comprising an organic acid from about 23% to about 75% surfactant; wherein said surfactant has an average ethoxylate/alkyl ratio of from about 0.001 to about 0.45; from about 10% to about 50% water soluble polymer; and from about 1% to about 15% plasticizer; and wherein said article has a density of from about 0.03 g/cm³ to about 0.20 g/cm³.

According to another embodiment, the hair care compositions may be in the form of a viscous liquid comprising a chelant; a buffer system comprising an organic acid from 5-20% surfactant and a polycarboxylate rheology modifier; wherein the polycarboxylate is specifically chosen to be effective at the high electrolyte levels resulting from the incorporation of the key buffer system and chelant required for this invention. Non-limiting examples include acrylates/C10-C30 alkyl acrylate crosspolymers such as Carbopol EDT2020, 1342, 1382, etc. from Lubrizol. Rheology benefits of these actives in our embodiments include stability, ease of dispensing, smoothness of spreading, etc.

The hair care compositions are generally prepared by conventional methods such as are known in the art of making the compositions. Such methods typically involve mixing of the ingredients in one or more steps to a relatively uniform state, with or without heating, cooling, application of vacuum, and the like. The compositions are prepared such as to optimize stability (physical stability, chemical stability, photostability) and/or delivery of the active materials. The hair care composition may be in a single phase or a single product, or the hair care composition may be in a separate phases or separate products. If two products are used, the products may be used together, at the same time or sequentially. Sequential use may occur in a short period of time, such as immediately after the use of one product, or it may occur over a period of hours or days.

EXAMPLES

The following examples illustrate embodiments of the invention described herein. The exemplified shampoo compositions, conditioner compositions, and/or leave-on treatments can be prepared by conventional formulation and mixing techniques. It will be appreciated that other modifications of the shampoo compositions, conditioner compositions, and/or leave-on treatments within the skill of those in the formulation art can be undertaken without departing from the spirit and scope of this invention. All parts, percentages, and ratios herein are by weight unless otherwise specified. Some components may come from suppliers as dilute solutions. The amount stated reflects the weight percent of the active material, unless otherwise specified.

The following are non-limiting examples of shampoo compositions, conditioner compositions, and leave-on treatments described herein.

Shampoo Examples

| Components | Ex. 1 | Ex. 2 | Ex. 3 | Ex. 4 | Ex. 5 | Ex. 6 | Ex. 7 |
|---|---|---|---|---|---|---|---|
| sodium lauryl ether sulfate (SLE3S) | — | 6 | 10 | 6 | 6 | 9 | — |
| Sodium cocoyl isethionate | — | — | — | — | — | — | 8.5 |
| sodium lauryl sulfate (SLS) | 1.5 | 7 | 1.5 | 7 | 7 | 6 | — |
| sodium lauryl ether sulfate (SLE1S) | 10.5 | — | — | — | — | — | — |
| Disodium laureth sulfosuccinate | — | — | — | — | — | — | 8.5 |
| Sodium lauryl sulfoacetate | — | — | — | — | — | — | 2.5 |
| Sodium Lauroyl Sarcosinate | — | — | — | — | — | — | 0.75 |
| Cocoamidopropyl Hydroxysultaine | — | — | — | — | — | — | 1.5 |
| Cocoamidopropyl Betaine | 1 | 2 | 2 | 2 | 2 | 2 | 2 |
| Coconut monoethanol amide (CMEA) | — | 0.85 | — | 0.85 | — | — | — |
| Cetyl alcohol | — | — | 1 | — | — | — | — |
| Stearyl alcohol | — | — | 2 | — | — | — | — |
| dimethicone | 1 | 1 | 1 | 1 | 1 | — | 0.5 |
| Ethylene glycol distearate (EGDS) | 1.5 | 1.5 | 1.5 | 1.5 | 1.5 | — | — |
| Jaguar ® C500[1] | 0.25 | 0.25 | 0.15 | — | — | — | — |
| Synthetic Cationic Polymer AMT[2] | — | — | — | 0.1 | — | — | — |
| Polydiallyldimethylammonium chloride (DADMAC) | — | — | — | — | 0.1 | — | — |
| Excel Guar[3] | — | — | — | — | — | 0.1 | .15 |
| Ethylene diamine disuccinic acid (EDDS) | 0.1 | — | 0.1 | — | — | 0.1 | — |
| Histidine | — | 0.1 | — | 0.1 | 0.05 | — | 0.1 |
| pH | 6 | 6 | 6 | 6 | 6 | 6 | 6 |
| Water-USP Purified & Minors | Q.S. to 100 | Q.S. to 100 | Q.S. to 100 | Q.S. to 100 | Q.S. to 100 | Q.S. to 100 | Q.S. to 100 |

[1] Cationic polymer derived from a natural gum with low aqueous viscosity

[2] Cationic synthetic copolymer

[3] Cationic plant derived polymer

| Ingredient | Ex. 8 | Ex. 9 | Ex. 10 | Ex. 11 |
|---|---|---|---|---|
| Water-USP Purified & Minors | Q.S. to 100 | Q.S. to 100 | Q.S. to 100 | Q.S. to 100 |
| Sodium Laureth Sulfate (SLE1S) | 12 | 14 | 12 | 14 |
| Sodium Lauryl Sulfate (SLS) | 1.5 | | 1.5 | |
| Cocoamidoproply Betaine (CapB) | 1.7 | 1.7 | 1.7 | 1.7 |
| Gel Network | 1.0 | 1.0 | 2.0 | 2.0 |
| Guar Hydroxypropyltrimonium Chloride | 0.3 | 0.3 | 0.3 | 0.3 |
| Polyquaternium 6 (DADMAC) | 0.1 | 0.1 | 0.1 | 0.1 |
| Ethylene Glycol Distearate | 1.5 | | 1.5 | |
| Trihydroxy Stearin (Thixcin) | | 0.1 | | 0.1 |
| Dimethicone/Dimethiconol | 1.0 | 1.0 | 0.5 | 0.5 |
| Citric Acid | 1.0 | 1.0 | 1.0 | 1.0 |
| Sodium Citrate-Dihydrate Acrylates/C10-C30 alkyl acrylate crosspolymers | 1.0 | 1.0 | 1.0 | 1.0 |
| | | 0.3 | | |
| Histidine | 0.05 | 0.1 | 0.05 | 0.1 |
| Kathon | 0.0005 | 0.0005 | 0.0005 | 0.0005 |
| Sodium Benzoate | 0.25 | 0.25 | 0.25 | 0.25 |
| Disodium EDTA | 0.1274 | 0.1274 | 0.1274 | 0.1274 |
| Perfume | 0.8 | 0.8 | 0.8 | 0.8 |
| Sodium Chloride[1] | 0-3 | 0-3 | 0-3 | 0-3 |
| Sodium Xylene Sulfonate[1] | 0-3 | 0-3 | 0-3 | 0-3 |

[1]Levels adjusted to reach desired viscosity

Conditioner Examples

| Components | Ex. 1 | Ex. 2 | Ex. 3 | Ex. 4 | Ex. 5 | Ex. 6 |
|---|---|---|---|---|---|---|
| Water-USP Purified & Minors | QS to 100% | QS to 100% | QS to 100% | QS to 100% | QS to 100% | QS to 100% |
| BTMS[1] | 2.3 | 2.3 | 2.3 | 2.3 | 2.3 | 2.3 |
| BTMAC[2] | — | — | — | — | — | — |
| Cetyl alcohol | 1.1 | 1.1 | 1.1 | 1.1 | 1.1 | 1.1 |
| Stearyl alcohol | 2.8 | 2.8 | 2.8 | 2.8 | 2.8 | 2.8 |
| Soy Oligomer[3] | 1.0 | — | — | — | — | — |
| Soy Oligomer Blend[4] | — | 1.0 | — | — | — | — |
| Aminosilicone[5] | 1.0 | 1.0 | 1.0 | 1.0 | 2.0 | 2.0 |
| Perfume | 0.5 | 0.5 | 0.5 | 0.5 | 0.5 | 0.5 |
| Disodium EDTA | 0.1 | 0.1 | 0.1 | 0.1 | 0.1 | 0.1 |
| Panthenol | 0.03 | 0.03 | 0.03 | 0.03 | 0.03 | 0.03 |
| Panthenyl ethyl ether | 0.03 | 0.03 | 0.03 | 0.03 | 0.03 | 0.03 |
| Histidine | 0.05 | 0.10 | 0.10 | 0.10 | 0.05 | 0.10 |
| Benzyl Alcohol | 0.4 | 0.4 | 0.4 | 0.4 | 0.4 | 0.4 |
| Preservatives | 0.03 | 0.03 | 0.03 | 0.03 | 0.03 | 0.03 |

| Ingredients | Ex. 7 | Ex. 8 | Ex. 9 | Ex. 10 | Ex. 11 | Ex. 12 |
|---|---|---|---|---|---|---|
| Water-USP Purified & Minors | QS to 100% | QS to 100% | QS to 100% | QS to 100% | QS to 100% | QS to 100% |
| BTMS[1] | — | — | — | — | — | — |
| BTMAC[2] | 2.8 | 2.8 | 2.8 | 2.8 | 2.8 | 2.8 |
| Cetyl alcohol | 1.8 | 1.8 | 1.8 | 1.8 | 1.8 | 1.8 |
| Stearyl alcohol | 4.6 | 4.6 | 4.6 | 4.6 | 4.6 | 4.6 |
| Soy Oligomer[3] | — | — | 0.75 | — | — | — |
| Soy Oligomer Blend[4] | — | 1.0 | — | — | — | — |
| Aminosilicone[5] | 1.0 | — | 0.75 | 1.5 | 2.0 | 2.0 |
| Perfume | 0.5 | 0.5 | 0.5 | 0.5 | 0.5 | 0.5 |
| Disodium EDTA | 0.1 | 0.1 | 0.1 | 0.1 | 0.1 | 0.1 |
| Panthenol | 0.03 | 0.03 | 0.03 | 0.03 | 0.03 | 0.03 |
| Panthenyl ethyl ether | 0.03 | 0.03 | 0.03 | 0.03 | 0.03 | 0.03 |
| Histidine | 0.05 | 0.10 | 0.10 | 0.05 | 0.05 | 0.10 |
| Benzyl Alcohol | 0.4 | 0.4 | 0.4 | 0.4 | 0.4 | 0.4 |
| Preservatives | 0.03 | 0.03 | 0.03 | 0.03 | 0.03 | 0.03 |

| Ingredients | Ex. 13 | Ex. 14 | Ex. 15 | Ex. 16 |
|---|---|---|---|---|
| Water-USP Purified & Minors | QS to 100% | QS to 100% | QS to 100% | QS to 100% |
| BTMS[1] | 3.76 | 3.76 | 3.76 | 3.76 |
| BTMAC[2] | — | — | — | — |
| Cetyl alcohol | 1.3 | 1.3 | 1.3 | 1.3 |
| Stearyl alcohol | 3.2 | 3.2 | 3.2 | 3.2 |
| Soy Oligomer[3] | 1.0 | 1.0 | — | — |
| Soy Oligomer Blend[4] | — | — | — | — |
| Aminosilicone[5] | — | — | 1.0 | 1.0 |
| Perfume | 0.5 | 0.5 | 0.5 | 0.5 |
| Disodium EDTA | 0.1 | 0.1 | 0.1 | 0.1 |
| Panthenol | — | — | — | — |
| Panthenyl ethyl ether | — | — | — | — |
| Histidine | 0.10 | 0.05 | 0.05 | 0.10 |
| Benzyl Alcohol | 0.4 | 0.4 | 0.4 | 0.4 |
| Preservatives | 0.03 | 0.03 | 0.03 | 0.03 |
| Deposition Aid polymer[6] | 0.5 | — | 0.5 | — |

[1]Behenyltrimethylammonium methylsulfate, from Feixiang
[2]Behenyltrimethylammonium chloride, Genamin KDMP, from Clariant
[3]HY-3050, from Dow Corning
[4]HY-3051, from Dow Corning
[5]Y-14945; 10,000 cps aminodimethicone, from Momentive
[6]ABC1459 from Mitsubishi Chemical

Leave on Treatment Examples

| Components | Ex. 1 | Ex. 2 | Ex. 3 |
|---|---|---|---|
| Dipropyleneglycol Monomethylether | 0.500 | 0.500 | 0.500 |
| Disodium Ethylene diamine diacetic acid | 0.141 | 0.141 | 0.141 |
| PEG-40 Hydrogenated Castor Oil | 0.500 | 0.500 | 0.500 |
| Polysorbate 80[1] | 0.120 | 0.120 | — |
| Amodimethicone and Cetrimonium Chloride | 1.810 | 1.810 | 1.928 |
| Polyquaternium 11[2] | 1.335 | 1.335 | 1.335 |
| Citric Acid Anhydrous | 0.080 | 0.080 | 0.20 |
| 2-Amino-2-methyl-1-propanol | 0.100 | 0.100 | 0.100 |
| DMDM Hydantoin (55%)[3] | 0.370 | — | — |
| Benzyl Alcohol | — | 0.400 | 0.4 |
| Neolone 950 Preservative[4] | — | 0.053 | 0.053 |
| Perfume | 0.200 | 0.200 | 0.10 |
| Ethylene diamine disuccinic acid (EDDS) | 0.100 | 0.500 | — |
| Water-USP Purified & Minors | QS to 100% | QS to 100% | QS to 100% |

[1]Nonionic surfactant and emulsifier derived from polyethoxylated sorbitan and oleic acid
[2]Copolymer of vinylpyrrolidone and quaternized dimethylaminoethyl methacrylate
[3]1,3-Bis(hydroxymethyl)-5,5-dimethylimidazolidine-2,4-dione
[4]Preservative containing Methylisothiazolinone Data Shampoo Examples

| Component | A | B | C | D | E | F |
|---|---|---|---|---|---|---|
| sodium lauryl ether sulfate (SLE3S) | 6.0 | 6.0 | 6.0 | 6.0 | 6.0 | 6.0 |
| sodium lauryl sulfate (SLS) | 1.5 | 7.0 | 9.5 | 9.5 | 9.5 | 9.5 |
| sodium lauryl ether sulfate (SLE1S) | 10.5 | 10.5 | — | — | — | — |
| Cocoamidopropyl Betaine | 3.3 | 3.3 | 5.0 | 5.0 | 5.0 | 5.0 |
| Coconut monoethanol amide (CMEA) | 2.0 | 2.0 | — | — | — | — |
| dimethicone | 1.0 | 1.0 | — | — | — | — |
| Ethylene glycol distearate (EGDS) | 1.5 | 1.5 | — | — | — | — |
| Jaguar ® C500[1] | 0.25 | 0.25 | — | — | — | — |
| Sodium benzoate | 0.25 | 0.25 | 0.25 | 0.25 | 0.25 | 0.25 |
| Citric acid | 0.36 | 0.36 | — | — | — | — |
| Panthenol | 0.05 | 0.05 | 0.05 | 0.05 | 0.05 | 0.05 |
| Panthenyl ethyl ether | 0.03 | 0.03 | 0.03 | 0.03 | 0.03 | 0.03 |
| Tetrasodium ethylene diamine tetraacetic acid | 0.16 | 0.16 | 0.16 | 0.16 | 0.16 | 0.16 |
| Methylchloroisothiazolinone/ methylisothiazolinone | — | — | 0.03 | 0.03 | 0.03 | 0.03 |
| Ethylene diamine disuccinic acid (EDDS) | — | 0.10 | — | 0.10 | — | — |
| Histidine | — | — | — | — | 0.10 | — |
| Asparagine | — | — | — | — | — | 0.10 |
| pH | 6 | 6 | 6 | 6 | 6 | 6 |
| Water-USP Purified & Minors | Q.S. to 100 | Q.S. to 100 | Q.S. to 100 | Q.S. to 100 | Q.S. to 100 | Q.S. to 100 |

[1]Cationic polymer derived from a natural gum with low aqueous viscosity

Conditioner Examples

| Component | G | H | I | J |
|---|---|---|---|---|
| Citric acid | 0.13 | 0.13 | 0.13 | 0.13 |
| Stearamidopropyldimethyl-amine | 1.00 | 1.00 | 1.00 | 1.00 |
| Quaternium-18 | 0.75 | 0.75 | 0.75 | 0.75 |
| Hydroxypropyl guar (Jaguar HP105) | 0.35 | 0.35 | 0.35 | 0.35 |
| Cetyl alcohol | 1.20 | 1.20 | 1.20 | 1.20 |
| Stearyl alcohol | 0.80 | 0.80 | 0.80 | 0.80 |
| Non-ionic emulsifying wax (Polawax NF) | 0.50 | 0.50 | 0.50 | 0.50 |
| Glyceryl monostearate | 0.25 | 0.25 | 0.25 | 0.25 |
| Oleyl alcohol | 0.25 | 0.25 | 0.25 | 0.25 |
| Amino silicone[1] | 0.50 | 0.50 | 0.50 | 0.50 |
| Ethylenediamine tetraacetic acid | 0.10 | 0.10 | 0.10 | 0.10 |
| Benzyl alcohol | 0.40 | 0.40 | 0.40 | 0.40 |
| Kathon CG[2] | 0.03 | 0.03 | 0.03 | 0.03 |
| Histidine | — | 0.10 | — | — |
| Asparagine | — | — | 0.10 | — |
| Ethylene diamine disuccinic acid (EDDS) | — | — | — | 0.10 |
| pH | 6 | 6 | 6 | 6 |
| Water-USP Purified & Minors | Q.S. to 100 | Q.S. to 100 | Q.S. to 100 | Q.S. to 100 |

[1]Y-14945; 10,000 cps aminodimethicone, from Momentive
[2]Kathon CG-Combination of Methylchloroisothiazolinone with methylisothiazolinone Leave-on Treatment Examples

| Component | K | L |
|---|---|---|
| Amodimethicone & cetrimonium chloride | 1.93 | 1.93 |
| Polyquaternium-11 | 1.34 | 1.34 |
| PEG-40 hydrogenated castor oil | 0.50 | 0.50 |
| Benzyl alcohol | 0.40 | 0.40 |
| Trisodium ethylenediamine disuccinic acid | — | 0.50 |
| Citric acid | 0.20 | 0.20 |
| Methyl isothiazolinone | 0.05 | 0.05 |
| Panthenol | 0.09 | 0.09 |
| Panthenyl ethyl ether | 0.05 | 0.05 |
| Water-USP Purified & Minors | Q.S. to 100 | Q.S. to 100 |

Referring to Table 2, it was surprisingly found that a regimen (Leg 4) comprising (1) applying to and rising from the hair a shampoo composition comprising ethylenediamine-N,N'-disuccinic acid (EDDS), (2) applying to and rinsing from the hair a conditioner composition comprising histidine, and (3) applying to the hair a leave-on treatment comprising ethylenediamine-N,N'-disuccinic acid (EDDS) delivers better performance than the shampoo composition and conditioner composition together (Leg 3) or the shampoo composition alone (Leg 2) when used to remove copper from the hair and to inhibit copper deposition onto the hair.

TABLE 2

| Leg | | Cu AVG (ppm) | | | | |
|---|---|---|---|---|---|---|
| 1 (control) | Shampoo A | 72.56 | A | | | |
| 2 | Shampoo B | 52.08 | | B | | |
| 3 | Shampoo B + Conditioner H | 34.84 | | | C | |
| 4 | Shampoo B + Conditioner H + Leave on Treatment L | 21.04 | | | | D |

*Levels not connected by same letter are statistically different.

Now referring to Table 3, it was surprisingly found that a regimen comprising (1) applying to and rising from the hair a shampoo composition comprising ethylenediamine-N,N'-disuccinic acid (EDDS) or histidine, (2) applying to and rinsing from the hair a conditioner composition comprising histidine, and (3) applying to the hair a leave-on treatment comprising ethylenediamine-N,N'-disuccinic acid (EDDS) (Legs 4 & 5) delivers statistically better performance than:

(1) applying to and rising from the hair a shampoo composition comprising ethylenediamine-N,N'-disuccinic acid (EDDS), (2) applying to and rinsing from the hair a conditioner composition comprising ethylenediamine-N,N'-disuccinic acid (EDDS), and (3) applying to the hair a leave-on treatment comprising ethylenediamine-N,N'-disuccinic acid (EDDS) (Leg 2); and (1) applying to and rising from the hair a shampoo composition comprising asparagine, (2) applying to and rinsing from the hair a conditioner composition comprising asparagine, and (3) applying to the hair a leave-on treatment comprising ethylenediamine-N,N'-disuccinic acid (EDDS) (Leg 3).

The data presented in Table 3 is particularly surprising with regards to Leg 2 because, despite EDDS having the highest Formation Constant $K_{ML}$ for copper that is desired for efficient inhibition of deposition of copper (see Table 1), Legs 4 and 5 performed statistically better by replacing EDDS with histidine in the conditioner.

TABLE 3

| Leg | Shampoo | Conditioner | Treatment | Cu AVG (ppm) | Cu STDEV | Percent Cu Reduction | |
|---|---|---|---|---|---|---|---|
| 1 (control) | Shampoo C | Conditioner G | Leave on Treatment K | 73.967 | 7.6 | N/A | A |
| 2 | Shampoo D | Conditioner J | Leave on Treatment L | 42.267 | 5.0 | 42.9 | B |
| 3 | Shampoo F | Conditioner I | Leave on Treatment L | 42.767 | 4.5 | 42.2 | B |
| 4 | Shampoo E | Conditioner H | Leave on Treatment L | 27.367 | 3.5 | 63.0 | C |
| 5 | Shampoo D | Conditioner H | Leave on Treatment L | 22.433 | 2.3 | 69.7 | C |

*Levels not connected by same letter are statistically different.

Test Method I

"Test Method I" was used for Table 2, Legs 1 & 2.

Hair switches had been colored once with an oxidative hair colorant. An extra blonde shade was used for the testing. The hair switches were washed for 20 repeat wash cycles in tap water containing 7 grains per gallon water hardness (Ca/Mg) and 0.06 μg/g copper ions. Each wash cycle consisted of two applications of 0.1 g/g a shampoo to the hair switches. Each application consisted of adding shampoo to the hair, milking for 30 secs followed by rinsing for 30 secs. Shampoo was then reapplied 0.1 g/g, milked for 30 secs, rinsed for 30 secs and then dried in a heat box (60° C.) until dry.

Samples of 100 mg of hair were digested overnight with 2 ml of high purity concentrated nitric acid. The digestive mixture also contained 150 μL of 100 μg/g Yttrium internal standard (Inorganic Ventures, Christianburg, Va., USA). Following digestion, samples were heated to 70-80° C. for one hour, cooled to room temperature and diluted to 15 mL with deionized water. Copper content of the hair switches was determined by inductively coupled plasma atomic spectroscopy (ICP-OES)). For each leg, 3 different samples were analyzed.

Test Method II

"Test Method II" was used for Table 2, Leg 3.

Hair switches had been colored once with an oxidative hair colorant. An extra blonde shade was used for the testing. The hair switches were washed for 20 repeat wash cycles in tap water containing 7 grains per gallon water hardness (Ca/Mg) and 0.06 μg/g copper ions. Each wash cycle consisted of two applications of 0.1 g/g a shampoo to the hair switches. Each application consisted of adding shampoo to the hair, milking for 30 secs followed by rinsing for 30 secs. Excess water was squeezed from the hair switches and then 0.1 g/g of a conditioner was applied and milked for 30 secs and then rinsed for 30 seconds. The hair switches were dried in a heat box (60° C.) until dry.

Samples of 100 mg of hair were digested overnight with 2 ml of high purity concentrated nitric acid. The digestive mixture also contained 150 μL of 100 μg/g Yttrium internal standard (Inorganic Ventures, Christianburg, Va., USA). Following digestion, samples were heated to 70-80° C. for one hour, cooled to room temperature and diluted to 15 mL with deionized water. Copper content of the hair switches was determined by inductively coupled plasma atomic spectroscopy (ICP-OES)). For each leg, 3 different samples were analyzed.

Test Method III

"Test Method III" was used for Table 2, Leg 4 and Table 3, Legs 2-5.

Hair switches had been colored once with an oxidative hair colorant. An extra blonde shade was used for the testing. The hair switches were washed for 20 repeat wash cycles in tap water containing 7 grains per gallon water hardness (Ca/Mg) and 0.06 μg/g copper ions. Each wash cycle consisted of two applications of 0.1 g/g a shampoo to the hair switches. Each application consisted of adding shampoo to the hair, milking for 30 secs followed by rinsing for 30 secs. Excess water was squeezed from the hair switches and then 0.1 g/g of a conditioner was applied and milked for 30 secs and then rinsed for 30 seconds. Again excess water was squeezed from the hair and 0.1 g/g of Leave on Treatment applied and milked for 30 secs. The hair was dried in a heat box (60° C.) until dry.

Samples of 100 mg of hair were digested overnight with 2 ml of high purity concentrated nitric acid. The digestive mixture also contained 150 μL of 100 μg/g Yttrium internal standard (Inorganic Ventures, Christianburg, Va., USA). Following digestion, samples were heated to 70-80° C. for one hour, cooled to room temperature and diluted to 15 mL with deionized water. Copper content of the hair switches was determined by inductively coupled plasma atomic spectroscopy (ICP-OES)). For each leg, 3 different samples were analyzed.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of inhibiting copper deposition on hair and facilitating the removal of copper deposited on hair comprising:
   a. applying to the hair a shampoo composition comprising:
      i. from about 0.05% to about 0.2% of a compound selected from the group consisting of ethylenediamine-N,N'-disuccinic acid (EDDS), derivatives of ethylenediamine-N,N'-disuccinic acid (EDDS), salts of ethylenediamine-N,N'-disuccinic acid (EDDS), histidine, and mixtures thereof, by weight of the shampoo composition;
      ii. from about 2% to about 50% of one or more detersive surfactants, by weight of the shampoo composition; and
      iii. from about 20% to about 95% of a first aqueous carrier, by weight of the shampoo composition;
   b. rinsing the shampoo composition from the hair;
   c. applying to the hair a conditioner composition comprising:
      i. from about 0.05% to about 0.2% histidine, by weight of the conditioner composition;
      ii. a conditioner gel matrix comprising:
         1. from about 0.1% to about 20% of one or more high melting point fatty compounds, by weight of the gel matrix;
         2. from about 0.1% to about 10% of a cationic surfactant system, by weight of the gel matrix; and
         3. at least 20% of a second aqueous carrier, by weight of the gel matrix;
   d. rinsing the conditioner composition from the hair; and
   e. applying to the hair a leave-on treatment comprising:
      i. from about 0.25% to about 0.5% of a compound selected from the group consisting of ethylenediamine-N,N'-disuccinic acid (EDDS), derivatives of ethylenediamine-N,N'-disuccinic acid (EDDS), salts of ethylenediamine-N,N'-disuccinic acid (EDDS), and mixtures thereof, by weight of the leave-on treatment;
      ii. one or more rheology modifiers; and
      iii. at least 20% of a third aqueous carrier, by weight of the leave-on treatment.

2. The method of claim 1, wherein the conditioner composition comprises from about 0.1% to about 0.15% histidine, by weight of the conditioner composition.

3. The method of claim 1, wherein the conditioner composition further comprises one or more additional benefit agents.

4. The method of claim 3, wherein the one or more additional benefit agents is selected from the group consisting of anti-dandruff agents, vitamins, chelants, perfumes, brighteners, enzymes, sensates, attractants, anti-bacterial agents, dyes, pigments, bleaches, and mixtures thereof.

5. The method of claim 3, wherein the one or more additional benefit agents is an anti-dandruff agent.

6. The method of claim 1, wherein the shampoo composition has a pH of from about 3.5 to about 5.

7. The method of claim 1, wherein the shampoo composition has a pH of about 4.25.

8. The method of claim 1, wherein the shampoo composition has a pH of from about 5.25 to about 7.

9. The method of claim 1, wherein the first aqueous carrier is water.

10. The method of claim 1, wherein the shampoo composition comprises from about 0.1% to about 0.15% of a compound selected from the group consisting of ethylenediamine-N,N'-disuccinic acid (EDDS), derivatives of ethylenediamine-N,N'-disuccinic acid (EDDS), salts of ethylenediamine-N,N'-disuccinic acid (EDDS), histidine, and mixtures thereof, by weight of the shampoo composition.

11. The method of claim 1, wherein the shampoo composition further comprises one or more additional benefit agents.

12. The method of claim 11, wherein the one or more additional benefit agents is selected from the group consisting of anti-dandruff agents, vitamins, chelants, perfumes, brighteners, enzymes, sensates, attractants, anti-bacterial agents, dyes, pigments, bleaches, and mixtures thereof.

13. The method of claim 11, wherein the one or more additional benefit agents is an anti-dandruff agent.

14. The method of claim 1, wherein the shampoo composition comprises about 0.1% of the compound selected from the group consisting of ethylenediamine-N,N'-disuccinic acid (EDDS), derivatives of ethylenediamine-N,N'-disuccinic acid (EDDS), salts of ethylenediamine-N,N'-disuccinic acid (EDDS), histidine, and mixtures thereof, by weight of the shampoo composition; wherein the conditioner composition comprises about 0.1% histidine, by weight of the conditioner composition; and wherein the leave-on treatment comprises about 0.5% of the compound selected from the group consisting of ethylenediamine-N,N'-disuccinic acid (EDDS), derivatives of ethylenediamine-N,N'-disuccinic acid (EDDS), salts of ethylenediamine-N,N'-disuccinic acid (EDDS), and mixtures thereof, by weight of the leave-on treatment.

* * * * *